United States Patent [19]
Galy et al.

[11] Patent Number: 4,475,225
[45] Date of Patent: Oct. 2, 1984

[54] MEASURING INSTRUMENT FOR X-RAY STRUCTURE DETERMINATIONS OF LIQUID OR AMORPHOUS MATERIALS

[75] Inventors: Jean Galy; Alain Mosset; Pierre Lecante, all of Toulouse, France

[73] Assignee: Agence Nationale De La Valorisation De La Recherche (Anvar), Paris, France

[21] Appl. No.: 284,232

[22] Filed: Jul. 17, 1981

[30] Foreign Application Priority Data

Jul. 18, 1980 [FR] France .................. 80 16170

[51] Int. Cl.$^3$ ............................................. G01N 23/20
[52] U.S. Cl. ......................................... 378/88; 378/86
[58] Field of Search ............. 378/86, 88, 71, 70, 378/75, 80

[56] References Cited

U.S. PATENT DOCUMENTS 3,105,902  10/1963  Ostrofsky .......................... 378/80
4,076,981  2/1978   Sparks ................................ 378/71

FOREIGN PATENT DOCUMENTS 660703   11/1951  United Kingdom .
901650   7/1962   United Kingdom .
1099975  1/1968   United Kingdom .
1208923  10/1970  United Kingdom .
1402110  8/1975   United Kingdom .

OTHER PUBLICATIONS

A. Saint-Etienne "X-ray Residual Stress Measurement with a Position Sensitive Proportional Detextor" (translated title), Mecantique Materiaux Electricite, 1976, vol. 59 No. 318 et No. 319, pp. 39–41.

Primary Examiner—Craig E. Church
Attorney, Agent, or Firm—Cushman, Darby & Cushman

[57] ABSTRACT

The present invention relates to an instrument for measuring the variations in intensity of a beam of X-rays scattered by liquid or amorphous solid materials, which comprises: a goniometric head carrying said material and mounted rotationally movable, a position sensitive proportional detector mounted movable along a radial supporting arm, with a rotational motion which is coaxial to the motion of said goniometric head, and having an angular amplitude twice that of the angular change of location of said head, and a monochromator situated on the X-ray beam. Such an instrument is specially designed for liquid or amorphous solid materials, which only scatter an X-ray beam with a very low intensity. The monochromator or said instrument is located on the path of the beam of X-rays scattered by said liquid or amorphous solid material, after the latter and before said position sensitive proportional detector.

5 Claims, 1 Drawing Figure

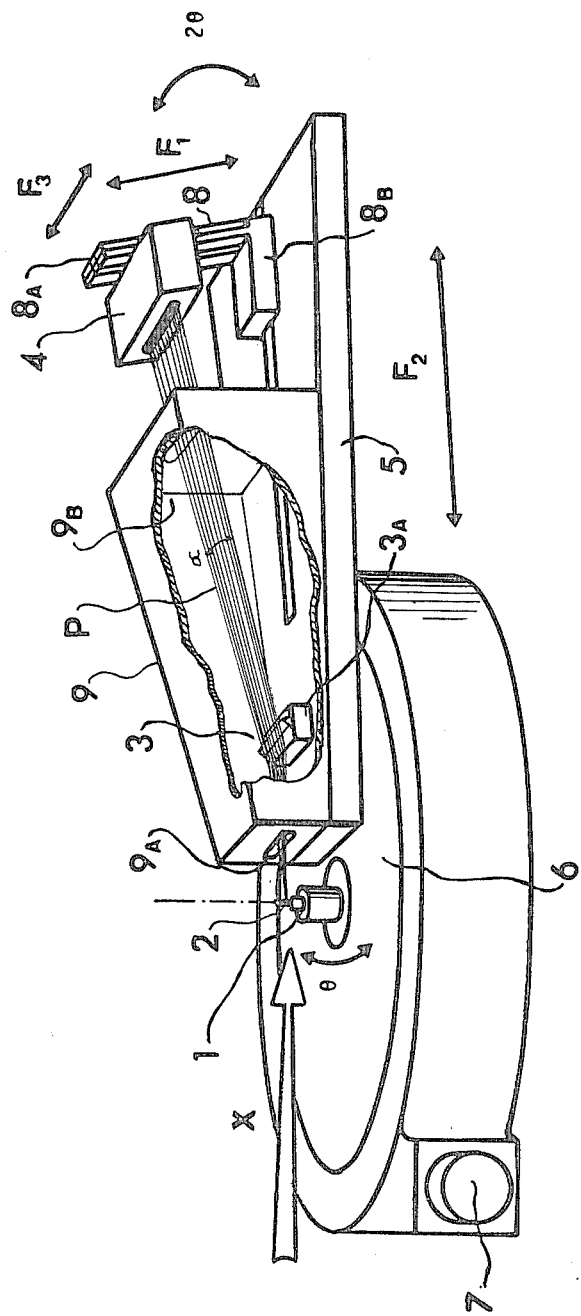

MEASURING INSTRUMENT FOR X-RAY STRUCTURE DETERMINATIONS OF LIQUID OR AMORPHOUS MATERIALS

BACKGROUND OF THE INVENTION

The study of X-ray scattering by amorphous or liquid compounds for the purpose of gathering informations allowing structure determinations of said compounds is carried out by means of an X-ray diffractometer which spot-registers the variations in intensity of the beam of X-rays scattered by the material tested. Such a process is time-taking as such positioning of said material requires successive changes of location of the diffractometer detector (scintillation counter) for spot-measuring and -registering of all the variations in intensity of said X-ray beam. E.g., the X-ray diffraction study of a liquid or amporphous solid material, carried out in a laboratory with a conventional automatic diffractometer requires 3–4 weeks for screening the full spectrum $2° \leq \theta \leq 80°$ (Bragg angle).

Such an analysis time is quite long and consequently affects the quality of the data registered. Especially, the "structure" of liquid or amorphous compounds is quite unstable, because of chemical or physical requirements, which consequently vitiates the interpretation of the data registered by the detector.

SUMMARY OF THE INVENTION

The measuring instrument of this invention allows considerable speeding up of the analysis time as it allows the suppression of the detector changes of location for an identical angle of incidence of an X-ray beam on the tested material. The instrument of the present invention comprises a position sensitive proportional detector, whose wire screens the whole variations in intensity of the beam of scattered X-rays. It thus allows to register the complete variations for the same position.

In order to screen the full spectrum ranging form 2° to 80° ($\theta$ Bragg angle), the said detector is mounted on a supporting arm movable step by step with a rotational motion coaxial to the motion of the tested material set on a goniometric head mounted rotational with an amplitude twice that of the angular change of location of the said material.

The measurements carried out with this instrument are much quicker (ca. 7–8 hrs.) which, further to palliating the above-cited drawbacks of conventional diffractometers, still save considerable time to the user, which is highly appreciated in the field of scientific research when the same experiment has to be carried out several times on the same kind of material, in order to check the accuracy of the results obtained.

Advantageously, the said detector is mounted movable on its supporting arm, along the axis connecting it to the center of rotation of the tested material. Such a mobility of the detector allows the adjustment of the distance separating the latter from the testing material, especially according to:

the resolving power of the detector
the nature of the material tested.

The data and the values of the intensities registered by the detector are only accepted for a precise wavelength of the X-ray source: consequently, the measuring instrument of the invention is equipped with a monochromator having a variable surface of diffraction, situated along the path of the beam of scattered X-rays, close to tested material, so as to comply with the instrumental conditions. The useful surface of this monochromator is determined according to the angle of reflection of the beam of scattered X-rays, so that the detector wire may be easily positioned in the plane of said beam, whatever the nature of the tested material and the angle of incidence of the beame may be. To further improve the adjustment of said wire in the plane of said beam, the height of the detector has been made variable with respect to the plane of the supporting arm.

The beam of scattered X-rays may travel through the air, but the constituents of ambient air are not necessarily transparent to such low wavelength electromagnetic radiations. Consequently, a further object of the invention is to provide optimum experimental conditions by means of a vaccum chamber jacketing the X-ray beam and equipped with two windows for the inlet and the outlet of said beam, respectively.

In a preferred embodiment of the invention, the monochromator is as well situated inside the vacumm chamber.

A still further object of the invention is to have the tested material centered on the rotational axis of the instrument of the invention by the mounting of a sighting instrument.

The present invention comprises further features which will be preferably used together with the main ones and which will be described hereafter.

DETAILED DESCRIPTION OF THE PREFERRED EMBODIMENTS

Further details as to preferred practices and as to further objects and features thereof may be most readily comprehended through reference to the following detailed description when taken in connection with the accompanying drawing.

The FIGURE of the drawing is a partially sectioned perspective view of the instrument of the invention, which comprises a goniometric head 1 carrying a liquid or amorphous solid material 2 whose structure is to be studied by undergoing a bombardment with an X-ray beam (arrow X). Under the incidence of this beam, the tested material 2 scatter and X-ray beam P which is then reflected on the plate of a monochromator 3 (e.g. made of graphite), and next fells upon the wire of a position sensitive proportional detector 4 intended for registering the variations in intensity of the X-ray beam, in the angle $\alpha$ of the latter.

The monochromator 3 and the detector 4 are adjusted on a supporting arm 5 fitted up on a stage 6 rotationally movable. The rotational motion $2\theta$ is coaxial to the rotational motion $\theta$ of the goniometric head 1. A step-by-step motor 7 provides simultaneous drive for both rotations. The monochromator 3 gives the beam P, once reflected, an angle in relation to the incident plane, defined as "a". Said "a" angle may vary with the nature of the material 2 and of the angle of incidence of the beam. Consequently, the plate of the monochromator 3 is adjustable on its support 3a and the detector is movable (arrow $F_1$) along the inclined pole or support 8a of a carriage 8, so that wire of the detector 4 may be adjusted inside the plane of the beam P reflecting on the monochromator, whatever the angle "a" may be.

Also, the base plate 8b of the carriage 8 on which the support 8a inclinably lies, may be moved (arrow $F_2$) along the arm 5 so as to make the distance covered by the beam P of X-rays between the material 1 and the wire of the detector 4, suitable both for the nature of said material and for the resolving power of said detector.

The mobility of the detector 4 along the arrow $F_1$ is of importance, as the height separating it from the plane of the arm 5 is directly proportional both to the "a" angle of the beam P and to the distance from the monochromator 3. This is expressed as:

$$h = L \cdot tg \cdot a$$

where h is said height, and L said distance.

It is a further object of the invention to have the detector 4 mounted on a support (not shown on the drawing), called "detector-carrier", so as to authorize the change of location of the detector along the arrow $F_3$, following an axis perpendicular to the bissectrix of the angle α. This change of location allows the precise positioning of the middle of the detector wire along said bissectrix. This characteristic is required by the X-ray beam shape, i.e. a right-angle triangle with the angle α at the apex; it is also further needed, as a better reading of the variations in intensity of said beam by the detector 4 is obtained if the wire of the latter is perpendicularly arranged on both sides of the bissectrix of the angle α.

As already stated in the present specification, the measuring instrument of the invention also comprises a vacuum chamber 9 surrounding part of the beam P and the monochromator 3. Said chamber 9 is tightly secured on the arm 5 and comprises two windows for the inlet and for the outlet of the beam P, 9a and 9b, respectively.

The angular range of α is taken equal to 12°; the same value is chosen for the change of location 2θ of the detector 4. The detector will consequently register all the variations in intensity of the beam P of X-rays scattered by the material 2, moving with a step of ca. 2/100° (depending upon the detector used).

No more than some 15 angular changes of location are needed for screening the full spectrum ranging from 2° to 80° (Bragg angle) and to get the full study of the X-ray scattering by a liquid or amorphous solid material.

Of course, the running of such a measuring instrument is controlled by a micro-computer for the determination, through predetermined data, of:

changes of location (θ–2θ) of the step-by-step motor 7 the input of data given by the detector 4 the storage, the processing, the scaling, etc . . . of the values of the intensities I(S) as a function of $S\pi 4 \sin \theta/\lambda$ (where λ is the wavelength of the X-ray beam) and the direct display on a screen of the experimental (or even theoretical radial distributions.

It should be understood that the specific embodiments and practices described in connection with this specification have been presented by way of disclosure rather than limitation, and that various modifications, combinations and substitutions may be effected by those skilled in the art without departure either in spirit or scope from this invention in its broader aspects and as set forth in the appended claims.

What we claim is:

1. An instrument for measuring the variations in intensity of the X-rays scattered by a liquid or an amorphous solid material, which only scatters an X-ray beam with a very low intensity, undergoing bombardment with a beam of X-rays, comprising:

an X-ray source, a goniometric head carrying said material and mounted rotationally movable, a position sensitive proportional detector mounted movable along a radial supporting arm, with a rotational motion which is coaxial to the motion of said goniometric head and having an angular amplitude twice that of the angular change of location of said head, and a monochromator, wherein said monochromator is located on the path of the beam of X-rays scattered by said liquid or amorphous solid material, after said material and before said position sensitive proportional detector wherein said detector is mounted movable along a horizontal axis perpendicular to the axis connecting it to the center of rotation of said material, and wherein the height of the detector separating it from the plane of said supporting arm is variable, and wherein the angle of incidence of said monochromator is adjustable.

2. A measuring instrument as set forth in claim 1, comprising a sighting instrument for centering said material on the rotational axis of said instrument.

3. A measuring instrument as set forth in claim 1, comprising a carriage movable along the supporting arm, said carriage having an inclinable support for the vertical motion of a detector-carrier along which the detector moves perpendicularly to the said support.

4. A measuring instrument as set forth in claim 1, comprising a vacuum chamber surrounding the beam of scattered X-rays, said chamber being equipped with two windows for the inlet and for the outlet of said beam, respectively.

5. A measuring instrument as set forth in claim 4, wherein said monochromator is located inside said vacuum chamber.

* * * * *